(12) United States Patent
Kitt

(10) Patent No.: US 10,966,891 B2
(45) Date of Patent: Apr. 6, 2021

(54) MEDICAL WORKSTATION MOUNTING APPARATUS

(71) Applicant: Keymed (Medical & Industrial Equipment) Ltd., Southend-on-Sea (GB)

(72) Inventor: David A. Kitt, Southend-on-Sea (GB)

(73) Assignee: Keymed (Medical & Industrial Equipment) Ltd., Southend on-Sea (GB)

( * ) Notice: Subject to any disclaimer, the term of this patent is extended or adjusted under 35 U.S.C. 154(b) by 0 days.

(21) Appl. No.: 16/889,991

(22) Filed: Jun. 2, 2020

(65) Prior Publication Data
US 2020/0383856 A1 Dec. 10, 2020

(30) Foreign Application Priority Data

Jun. 6, 2019 (GB) ...................................... 1908048

(51) Int. Cl.
*A61G 12/00* (2006.01)
(52) U.S. Cl.
CPC ......... *A61G 12/008* (2013.01); *A61G 12/001* (2013.01)
(58) Field of Classification Search
CPC .. A61G 12/008; A61G 12/001; A61G 12/005; A61G 7/0503; A47B 97/00; A47B 97/02; A47B 61/02; A47B 95/008; A47F 5/08; A47F 5/0807; A47F 5/0838; A47F 5/0846; A47F 5/0853; A47F 5/0884; A47F 7/0028; A47F 7/0021; B25H 3/04; A47L 13/512

USPC ......... 211/85.13, 87.01, 94.01, 94.02, 89.01, 211/60.1, 124, 66, 70.6, 75, 119.006, 211/119.007
See application file for complete search history.

(56) References Cited

U.S. PATENT DOCUMENTS

| | | | | |
|---|---|---|---|---|
| 944,312 A | * | 12/1909 | Brede ...................... | B25H 3/04 |
| | | | | 211/70.6 |
| 1,506,257 A | * | 8/1924 | Schmidt ................... | A47K 1/09 |
| | | | | 206/362.3 |

(Continued)

FOREIGN PATENT DOCUMENTS

| CN | 202627133 U | 1/2013 |
|---|---|---|
| EP | 3202387 A1 | 8/2017 |
| WO | WO 2018/013581 A1 | 1/2018 |

OTHER PUBLICATIONS

United Kingdom Intellectual Property Office, Search Report in United Kingdom Patent Application No. GB1908048.0, 1 p. (dated Nov. 5, 2019).

(Continued)

*Primary Examiner* — Jennifer E. Novosad
(74) *Attorney, Agent, or Firm* — Leydig, Voit & Mayer, Ltd.

(57) ABSTRACT

A medical workstation mounting apparatus comprises an elongate body with front and rear faces and configured for attachment to a shelf of a medical workstation. The apparatus has a length, a depth, and a thickness which is the distance between the front and rear faces. A plurality of accessory receivers extend from the body. Each receiver comprises a pair of arms with a channel between them configured to receive a hook of an accessory. The maximum thickness of the apparatus is less than its maximum depth to ensure a slim profile and compact shape.

10 Claims, 4 Drawing Sheets

(56) References Cited

U.S. PATENT DOCUMENTS

| | | | | |
|---|---|---|---|---|
| 2,028,694 A * | 1/1936 | Spinks | A47K 1/09 | 211/65 |
| 2,371,433 A * | 3/1945 | Davis | B25H 3/04 | 211/70.6 |
| 2,465,859 A * | 3/1949 | Fidler | A47G 25/0685 | 223/96 |
| 2,521,134 A * | 9/1950 | Stanitz | A47B 95/008 | 211/72 |
| 2,707,052 A * | 4/1955 | Brown | A47K 1/09 | 211/65 |
| 2,916,159 A * | 12/1959 | O'Neill | H01R 9/2608 | 211/89.01 |
| 3,990,755 A * | 11/1976 | Krause | A47K 5/18 | 312/207 |
| 4,094,415 A * | 6/1978 | Larson | A47F 5/0823 | 211/57.1 |
| 4,203,373 A * | 5/1980 | Conti | A47B 57/06 | 108/152 |
| 4,209,098 A * | 6/1980 | Adams | A01K 97/08 | 211/70.8 |
| 4,367,819 A * | 1/1983 | Lewis | A47G 25/0678 | 211/106.01 |
| 4,410,095 A * | 10/1983 | Dembicks | A47F 5/08 | 211/70.6 |
| 4,467,925 A * | 8/1984 | Ratzloff | B25H 3/04 | 211/103 |
| 4,583,647 A * | 4/1986 | Schinzing | A47B 81/007 | 211/60.1 |
| 4,602,756 A * | 7/1986 | Chatfield | A61G 7/0503 | 248/222.14 |
| 4,869,378 A * | 9/1989 | Miller | A47F 5/0853 | 211/94.01 |
| 4,871,074 A * | 10/1989 | Bryson | A45D 20/12 | 211/26 |
| 4,899,971 A * | 2/1990 | Elkin | A47F 5/0853 | 211/88.01 |
| 5,035,389 A * | 7/1991 | Wang | F16B 3/00 | 248/224.51 |
| 5,110,080 A * | 5/1992 | Rieman | A47B 96/1408 | 211/94.01 |
| D327,197 S * | 6/1992 | Belokin, Jr. | D6/567 | |
| 5,188,325 A * | 2/1993 | Hilty | A47F 7/06 | 211/30 |
| 5,332,107 A * | 7/1994 | Williams | A47K 5/18 | 132/309 |
| 5,472,167 A * | 12/1995 | Shillington | A47F 5/0853 | 211/94.01 |
| 5,687,856 A * | 11/1997 | Kendrena | A47F 5/0846 | 211/65 |
| 5,704,495 A | 1/1998 | Bale et al. | | |
| 5,740,927 A * | 4/1998 | Yemini | A47B 96/067 | 211/66 |
| 5,829,723 A * | 11/1998 | Brunner | A61M 5/1413 | 248/222.13 |
| D411,066 S * | 6/1999 | Romeo | D6/567 | |
| D414,210 S * | 9/1999 | Davis | D19/85 | |
| 5,979,675 A * | 11/1999 | Moriarty | B01L 9/54 | 211/119.003 |
| 6,305,557 B1 * | 10/2001 | Brooks | B25H 3/04 | 211/70.6 |
| 6,349,507 B1 * | 2/2002 | Muellerleile | A47F 5/0846 | 108/106 |
| 6,415,932 B1 * | 7/2002 | Fiscus | A47B 81/005 | 211/60.1 |
| 6,481,679 B1 * | 11/2002 | Bennett | A61G 13/101 | 248/223.41 |
| D468,591 S * | 1/2003 | Lillelund | D7/590 | |
| 6,626,445 B2 * | 9/2003 | Murphy | A61G 12/001 | 280/47.34 |
| 6,719,153 B2 * | 4/2004 | Heneveld | A47B 81/005 | 211/70.1 |
| 6,945,414 B1 * | 9/2005 | Stevens | A47F 5/0846 | 211/183 |
| 7,441,669 B1 * | 10/2008 | Dalbey | A47F 7/0028 | 211/85.7 |
| 7,464,907 B1 * | 12/2008 | Lane | A47K 1/09 | 211/75 |
| 7,562,883 B2 * | 7/2009 | Livengood | A61G 12/001 | 280/43.17 |
| D597,776 S * | 8/2009 | Taggart | D6/552 | |
| D608,054 S * | 1/2010 | Radfar | D28/73 | |
| 7,802,680 B2 * | 9/2010 | Krebs | B25H 3/04 | 206/349 |
| 8,245,992 B2 * | 8/2012 | Matsui | F16M 13/02 | 248/317 |
| 8,596,473 B2 * | 12/2013 | Newbould | A47K 1/09 | 211/88.01 |
| 8,640,890 B2 * | 2/2014 | Schiller | B65F 1/1415 | 211/85.15 |
| 8,646,625 B2 * | 2/2014 | Wang | A47G 25/06 | 211/106.01 |
| D743,048 S * | 11/2015 | Kuran | D24/231 | |
| 9,247,810 B2 * | 2/2016 | Metzler | A47B 57/045 | |
| 9,681,781 B2 * | 6/2017 | Hurley | F16B 47/003 | |
| 9,925,825 B1 * | 3/2018 | Hoffmann, IV | B44D 3/04 | |
| D852,538 S * | 7/2019 | Lawrence | D6/552 | |
| 2004/0079716 A1 * | 4/2004 | Hester | A47K 1/09 | 211/66 |
| 2004/0099624 A1 * | 5/2004 | Hein | B25H 3/04 | 211/89.01 |
| 2004/0251227 A1 | 12/2004 | Perkins et al. | | |
| 2005/0133473 A1 * | 6/2005 | Lesperance | A47B 81/005 | 211/64 |
| 2005/0247653 A1 * | 11/2005 | Brooks | B25H 3/04 | 211/94.01 |
| 2008/0053932 A1 * | 3/2008 | Newbould | A47B 55/02 | 211/88.01 |
| 2010/0044328 A1 * | 2/2010 | Barkdoll | A47F 5/0838 | 211/88.01 |
| 2010/0133218 A1 * | 6/2010 | Yang | A47K 3/281 | 211/119.009 |
| 2010/0327134 A1 | 12/2010 | Lundrigan et al. | | |
| 2011/0174752 A1 * | 7/2011 | Liao | A47F 5/0838 | 211/70.6 |
| 2011/0290965 A1 | 12/2011 | Virgin | | |
| 2013/0206938 A1 * | 8/2013 | Clouser | A47B 57/567 | 248/219.4 |
| 2014/0001325 A1 * | 1/2014 | Friesch | A63B 71/0045 | 248/231.9 |
| 2014/0049014 A1 | 2/2014 | Schumacher et al. | | |
| 2015/0060379 A1 * | 3/2015 | Larson | A47F 5/0884 | 211/71.01 |
| 2016/0000993 A1 * | 1/2016 | Endyk | A61B 5/008 | 211/85.13 |
| 2017/0037660 A1 | 2/2017 | Chesterton et al. | | |
| 2017/0188708 A1 * | 7/2017 | Yu | F16M 11/24 | |
| 2018/0228564 A1 | 8/2018 | Recanati et al. | | |
| 2018/0231176 A1 * | 8/2018 | Sabounjian | F16M 13/02 | |
| 2019/0069671 A1 * | 3/2019 | Williams | A47B 73/006 | |

OTHER PUBLICATIONS

European Patent Office, European Search Report in European Patent Application No. 20176856, 2 pp. (dated Aug. 18, 2020).

* cited by examiner

MEDICAL WORKSTATION MOUNTING APPARATUS

CROSS-REFERENCE TO RELATED APPLICATIONS

This patent application claims the benefit of United Kingdom Patent Application No. 1908048.0, filed Jun. 6, 2019, which is incorporated herein by reference in its entirety for all purposes.

BRIEF SUMMARY OF THE INVENTION

The present invention relates to a mounting apparatus enabling a variety of different accessories to be removably mounted on a mobile workstation used to carry medical equipment.

In medical environments, it is common to use a mobile workstation in the form of a wheeled trolley with multiple shelves to hold medical equipment. For example, this might be endoscopy equipment and associated accessories such as a power and light source, monitors for viewing, fluid pumps with associated tubing etc. Large items are typically placed on the workstation shelves. Frequently, it is also necessary to use a number of smaller accessories, such as bottles containing irrigation fluid, but there may be insufficient space for them on the shelves. The equipment will normally include multiple cables and tubing which can easily catch by mistake on parts of the workstation or other items of equipment when being moved.

The present invention provides medical workstation mounting apparatus for mounting accessories to a medical workstation, the apparatus comprising an elongate body with front and rear faces and configured for attachment to a shelf of a medical workstation, the apparatus having a length, a depth and a thickness, wherein the thickness is the distance between the front and rear faces, a plurality of accessory receivers extending from the body, each receiver comprising a pair of arms defining between them a channel configured to receive a hook of an accessory, wherein the apparatus has a maximum thickness which is less than its maximum depth.

The invention provides a universal mounting apparatus allowing a variety of different accessories to be mounted on a workstation, to suit the procedure being carried out. The accessories are held securely in convenient locations but can be moved or replaced easily and quickly without the need for any additional tools. The mounting apparatus itself is easily removable for cleaning and disinfection. It provides a standard interface that can accommodate multiple types of accessories. The mounting apparatus has a slim profile and compact shape, so that it extends only a small distance beyond the edge of a workstation shelf, and has no sharp corners or extensions, to minimise the risk of catching on cables or tubing or even the user's clothing.

Preferably each arm comprises a proximal portion extending forward of the elongate body and a distal portion extending parallel to the elongate body. The distal portion of each arm preferably extends towards the distal portion of the other arm of the pair. A slot is defined between the distal ends of the arms, in communication with the channel. These features maintain the slim profile of the apparatus and ensure a small thickness, keeping the apparatus compact and avoiding parts which stick straight out to form snagging risks.

Typically two accessory receivers are provided, located at opposite ends of the elongate bar.

Preferably there are a plurality of openings in the elongate body to receive mechanical fixing devices to attach the apparatus to the edge of a shelf of a medical workstation.

The elongate body may comprise a protruding portion configured to define an additional channel behind the body when installed on a shelf. The protruding portion protrudes forward no further than the accessory receivers so that it does not increase the overall thickness of the apparatus.

The mounting apparatus may be formed as an integral moulding.

The present invention also provides a medical workstation comprising a trolley with at least one shelf, and a mounting apparatus as claimed in any proceeding claim attached to the shelf.

BRIEF DESCRIPTION OF THE SEVERAL VIEWS OF THE DRAWINGS

The invention will now be described in detail, by way of example only, with reference to the accompanying drawings in which.

DETAILED DESCRIPTION OF THE INVENTION

Figure 1:
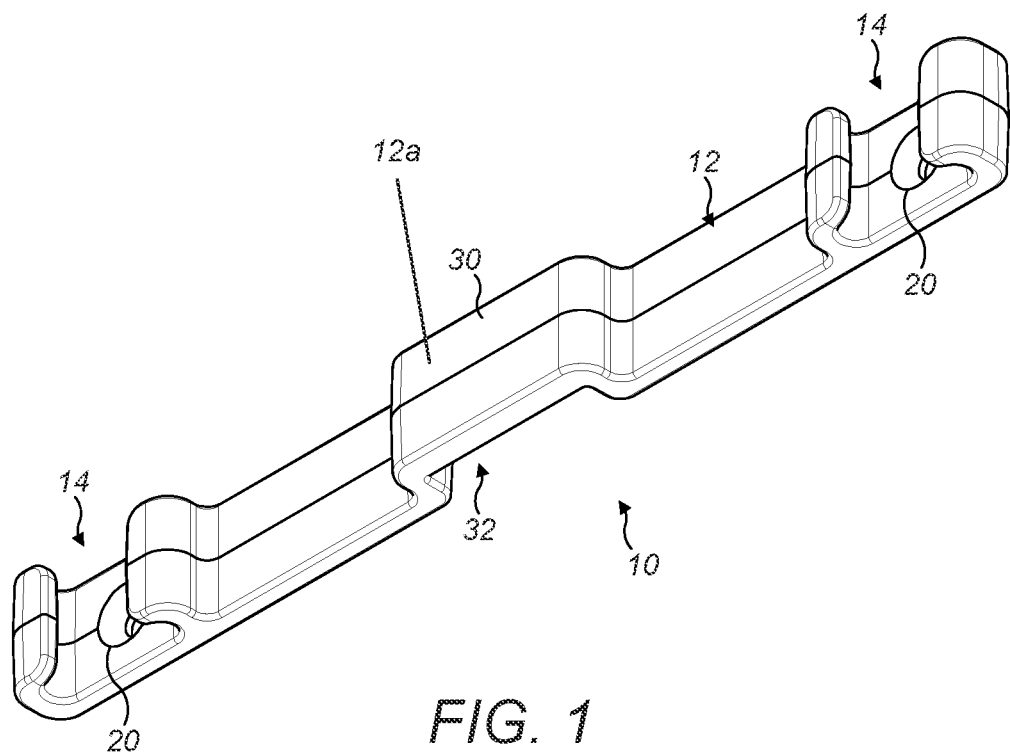
FIG. 1 is a perspective view of one embodiment of mounting apparatus, from the front and below.
Figure 2:
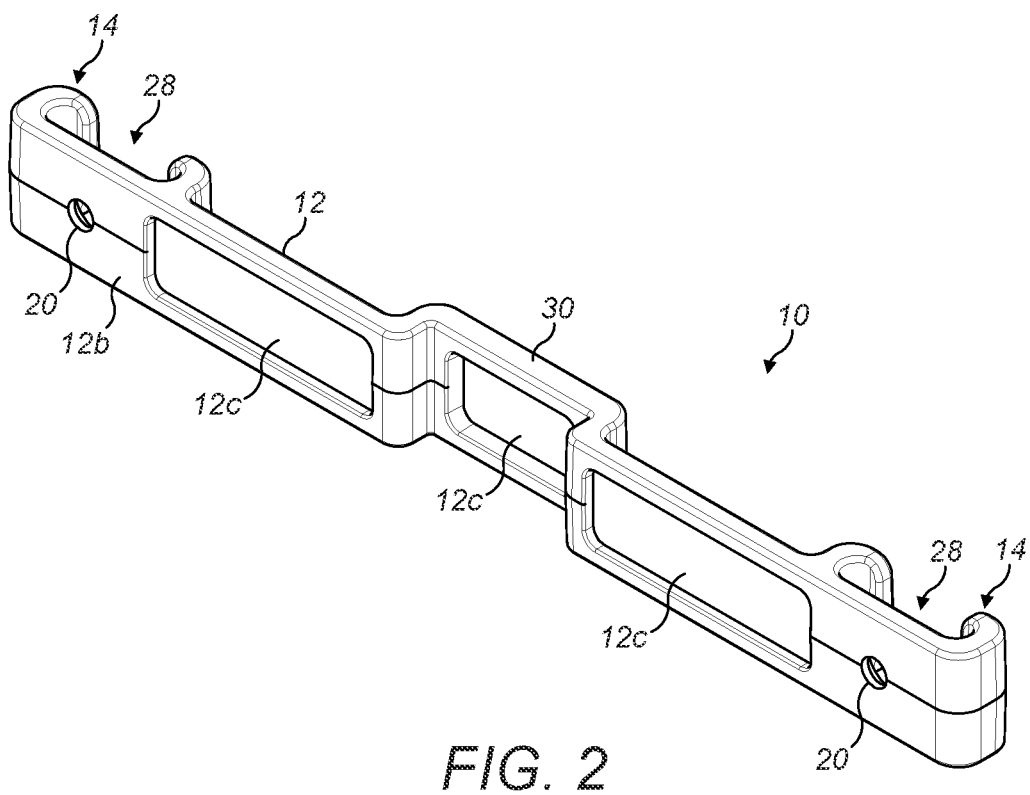
FIG. 2 is another perspective view of the rail of FIG. 1, from behind and above.
Figure 3:
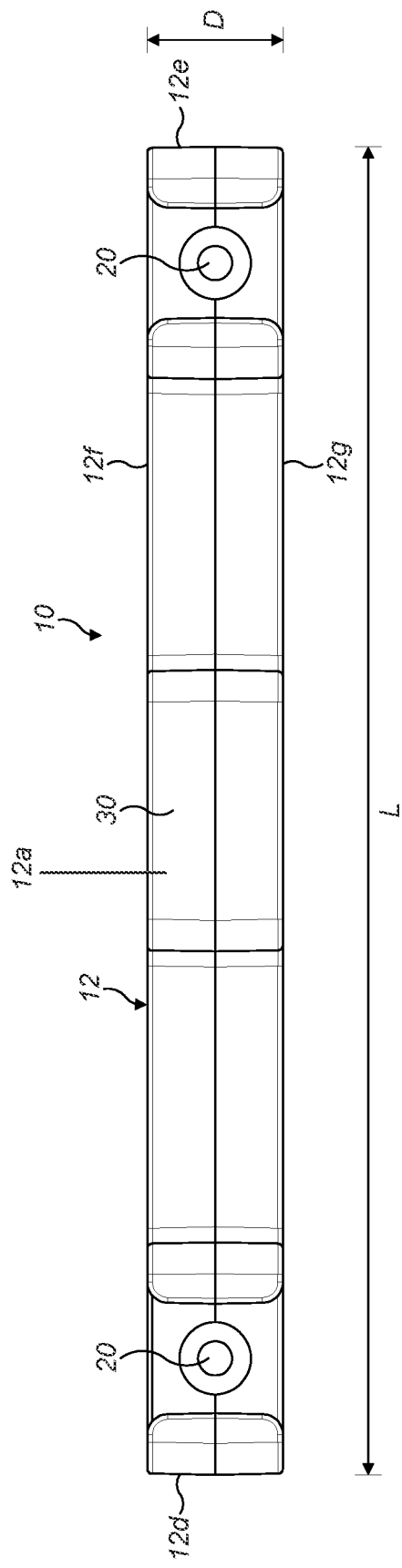
FIG. 3 is a front view of the apparatus of FIG. 1.
Figure 4:
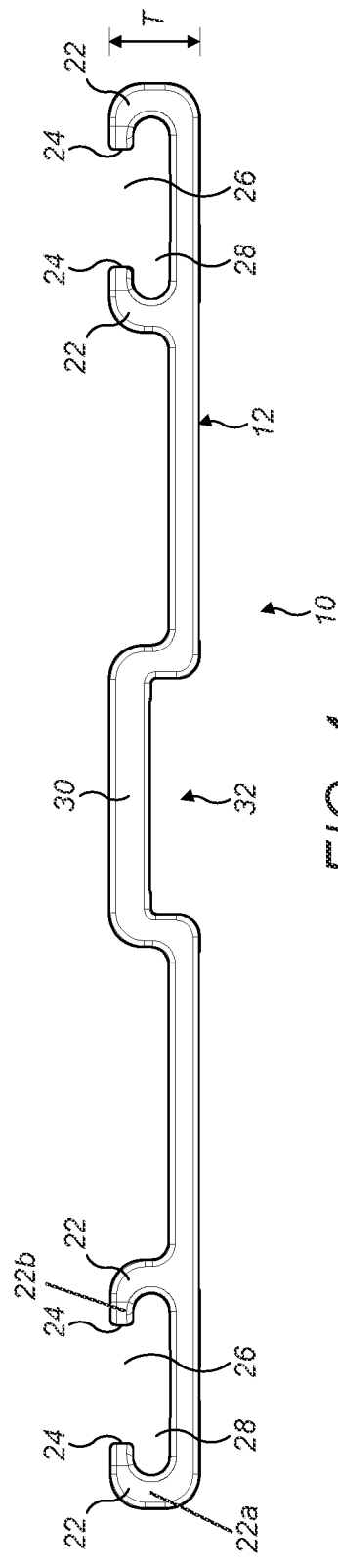
FIG. 4 is a plan view of the apparatus of FIG. 1.

As best seen in FIGS. 1 to 4, a first embodiment of a mounting apparatus or rail 10 comprises an elongate body or bar 12. It is generally flat, with a front face 12a, rear face 12b. The rear face 12b may feature recessed areas 12c to reduce the amount of material used and the overall weight of the rail 10. The rail 10 has a length L between its ends 12d, 12e, a depth D between its upper and lower edges 12f, 12g and a thickness T between the front and rear faces 12a, 12b. It is intended to be mounted with the length L extending horizontally and the depth D vertically. The thickness T represents the distance the rail 10 will extend out from a workstation shelf when fitted as discussed further below.

The bar 12 is integrally formed with a plurality of accessory receivers 14. In this case, two accessory receivers 14 are provided, located at opposite ends of the bar 12, although more than two may be provided if required. Typically, the mounting rail 12 and receivers 14 are substantially rigid and formed as a single integral moulding, of plastic or other suitable material. In this embodiment, the depth D is constant over the whole length L of the rail 10.

Figure 5:
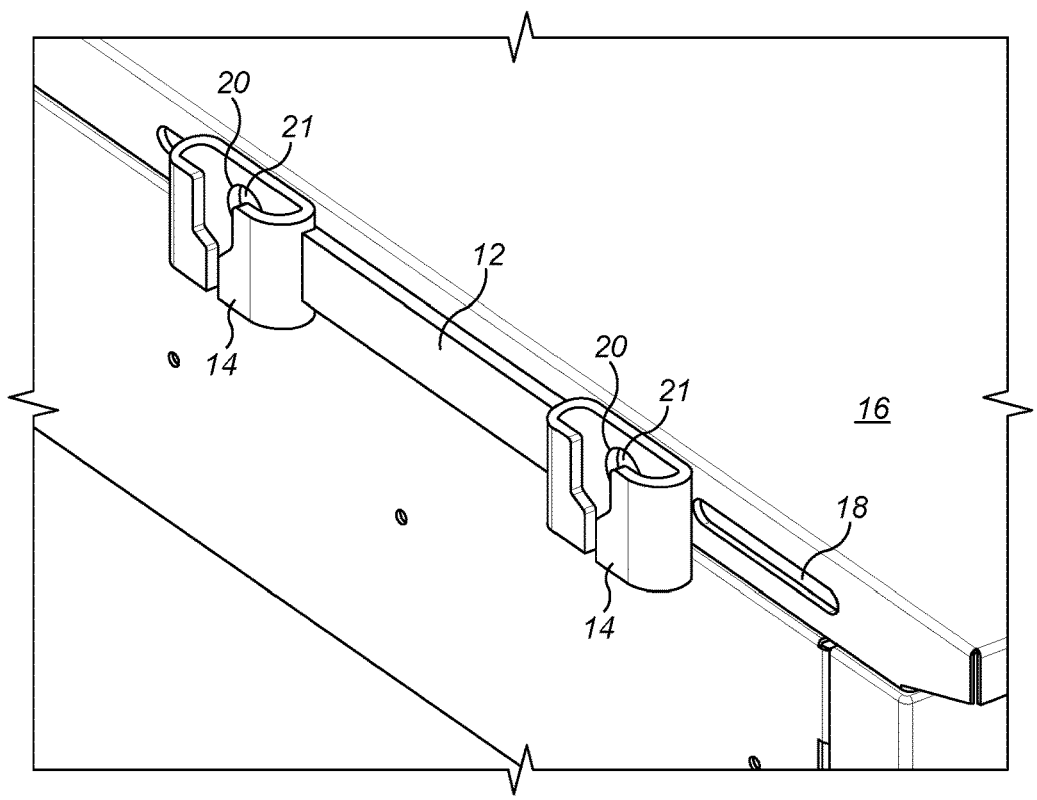
FIG. 5 is a perspective view of a second embodiment of mounting apparatus, attached to a workstation shelf.

The rail 10 is releasably securable to the edge of a shelf 16 of a medical workstation. The shelf 16 is provided with one or more openings 18. In the example in FIG. 5, elongate slots in the side of the shelf 16 are provided. The rail 10 is mountable to a shelf 16 by any convenient means, such as bolts or hooking members, which can pass through the openings 18. Preferably, the rail 10 is provided with a pair of fixing holes 20 through which bolts 21 can pass, to be secured by nuts (not visible) beneath the shelf 16. The fixing holes 20 may be chamfered so that a bolt head can sit flush with the front face 12b of the bar 12 when installed on a workstation. The fixing holes 20 are preferably arranged at opposite ends of the bar 12 to ensure it remains level when mounted on the shelf 16. The thickness T will be the distance the rail 10 extends out from the edge of the shelf 16.

Each accessory receiver 14 can be formed in a number of different shapes but in the first embodiment consist of two opposing arms 22 protruding from the bar 12. In plan view, the arms 22 are generally L-shaped, with a first, proximal portion 22a extending out substantially perpendicular to the bar 12 and then turning at a right angle so that a second, distal portion 22b extends substantially parallel to the bar 12. The arms 22 are arranged in pairs and the respective second portions 22b turn in to face each other so that the arms 22 do not stick straight out. In this way the rail 10 has a slim profile in plan view, i.e. a small thickness T between its front and rear faces. All the edges and corners of the rail 10 are radiussed or chamfered so that there no sharp edges or protrusions. Thus, the rail 10 has an overall smooth exterior and occupies a minimum space envelope, to provide a sleek appearance and to avoid any features sticking out that could catch or snag accidentally on other items such as cables or tubing, or cause injury to a person who knocked against it.

The distal ends 24 of the arms 22 do not meet each other, but are spaced apart leaving a slot 26 between them. In this embodiment, the fixing holes 20 are located between the arms 22 of each accessory receiver 14 and are therefore accessible through the slot 26. The arms 22 and bar 12 together define a vertical channel 28, open at the top and bottom and communicating with the slot 26, for receiving part of an accessory.

The bar 12 may also include a protruding region 30, as shown in FIGS. 1-4, stepped out from the adjacent areas of the bar 12. Preferably this region 30 is centrally located, between the accessory receivers 14, and extends forward no further than the receivers 14, to maintain the slim profile and small thickness T in plan view. The region 30 extends substantially parallel to the rest of the bar 12. The region 30 stiffens and strengthens the elongate bar 12. When installed on a workstation shelf 16, the protruding region 30 also defines another generally rectangular opening 32 behind the protruding region 30, between the rear face 12b and the shelf 16, which serves as an extra location for hooking other items onto the rail 10.

In use, the accessory receivers 14 receive hooks 34 provided on a medical accessory 36. Typically, such a hook 34 will have a main tab 38 (seen in FIGS. 6 and 8) which will be received in the channel 28 defined by the arms 22 and rail 12. Frequently, accessories may include a vertical strengthening rib 40 between the main body of the accessory and the vertical tab 38 (seen in FIG. 8). If this rib 40 is present, it will locate in the slot 26 between the free ends 24 of the arms 22.

Figure 6:
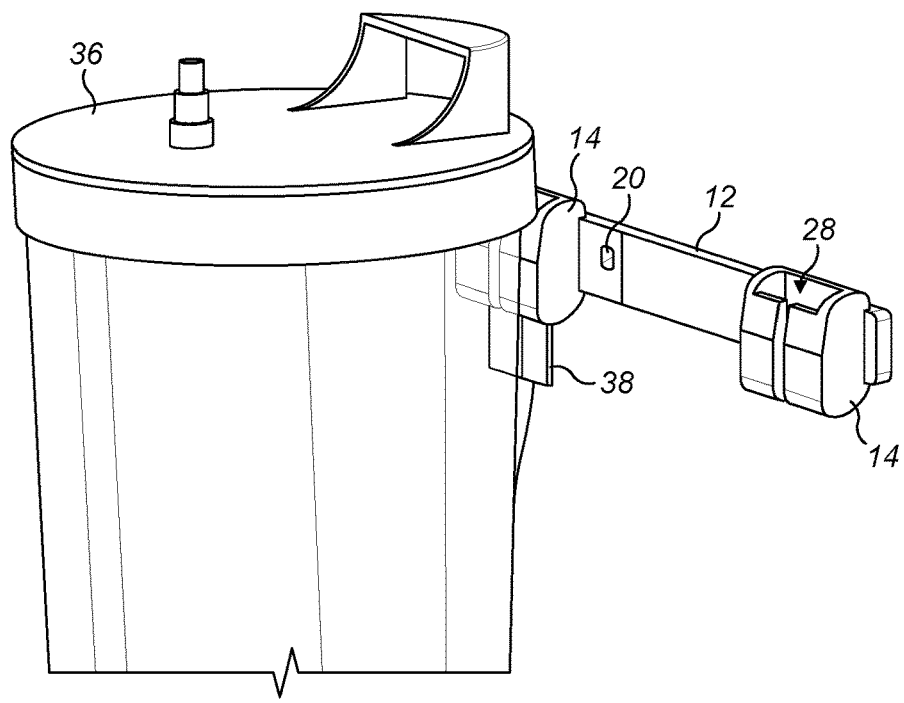
FIG. 6 is a perspective view of an accessory mounted on another embodiment of mounting apparatus.

The accessory 34 may engage in only one accessory receiver 14, such that the mounting rail 10 can accommodate two accessories 34 side by side. This may be suitable when the accessory comprises a smaller item such as a container for water or other irrigation fluid as shown in FIG. 6.

Figure 7:
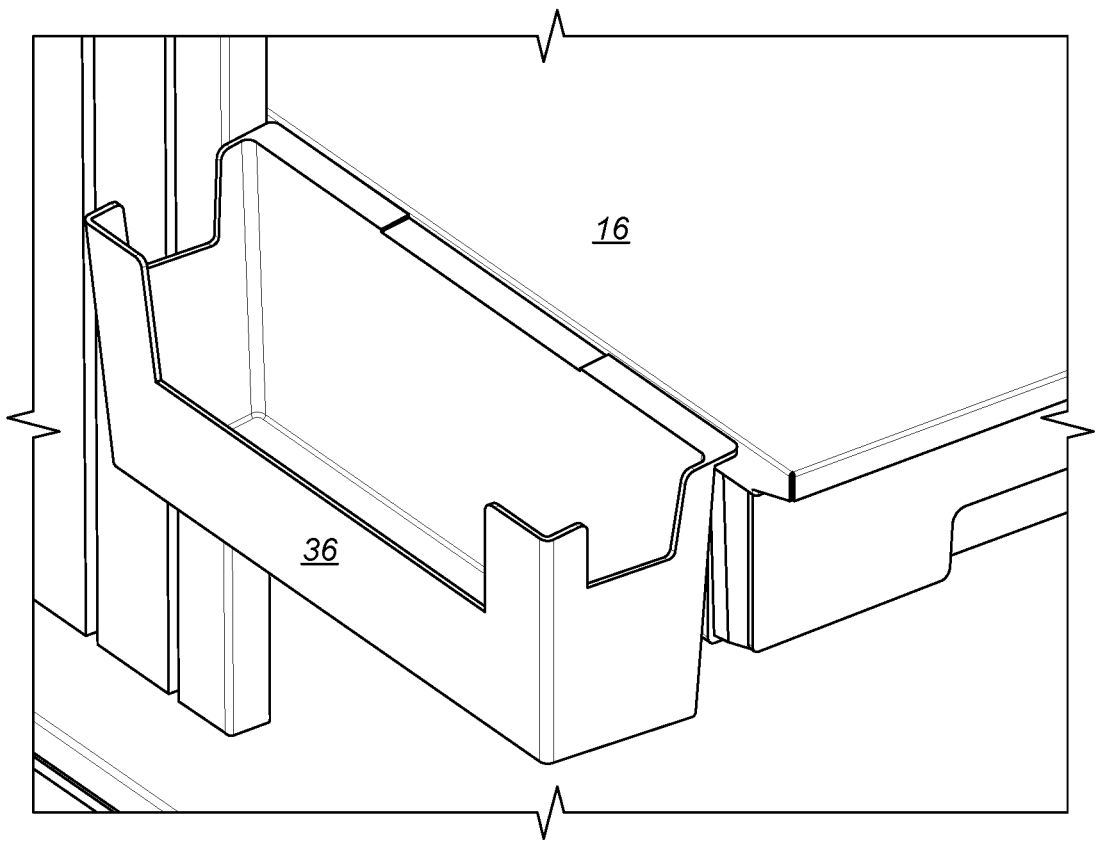
FIG. 7 is a perspective view of an alternative accessory mounted on a workstation.
Figure 8:
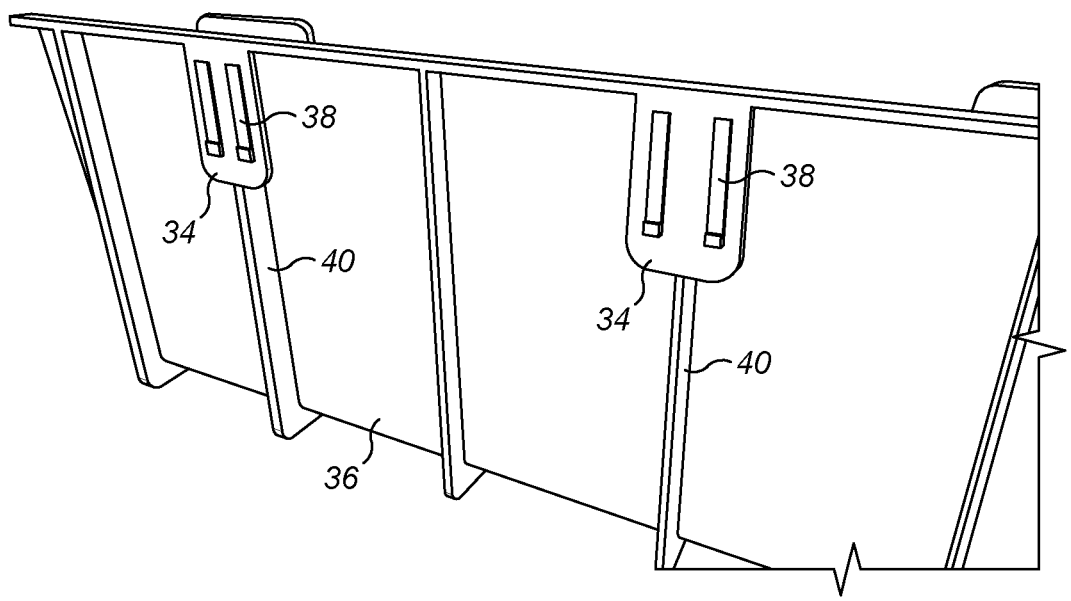
FIG. 8 is a rear view of the alternative accessory.

Alternatively, a larger, wider accessory 36 such as a stowage bin as shown in FIGS. 7 & 8 may have two hooks 34 for engaging both accessory receivers 14 on a rail 10, so that it can be securely mounted in a level configuration.

The length L of the mounting rail 10, and the spacing of the accessory receivers 14, will be sufficient to accommodate at least two accessories side by side, or a single wider accessory with two or more hooks. The smooth profile and small thickness T ensures the rail 10 is compact and keeps the accessories mounted close to the workstation.

As will be apparent from the Figures, the precise shape of the mounting rail 10 may be altered without departing from the scope of the invention. For example, in the embodiment shown in FIG. 5, the bar 12 has a smaller depth D in the region between the pair of accessory receivers 14. The distal ends 24 of the arms 22 of the accessory receivers 14 are also shaped to provide a slot 26 which is wider at the top and has a narrowed portion at the bottom. In the embodiment shown in FIG. 6, the fixing holes 20 for attachment of the rail 10 to the workstation are provided adjacent to the accessory receivers 14 rather than within them, so that the holes are more easily accessible. In the embodiments of both FIGS. 5 and 6, the bar 12 is flat and is not formed with the central protruding region 30.

The invention claimed is:

1. A medical workstation mounting apparatus for mounting accessories to a medical workstation, the apparatus comprising an elongate body and defining front and rear faces, the medical workstation mounting apparatus being configured for attachment to a shelf of a medical workstation along said rear face, the apparatus having a length, a depth and a thickness, wherein the thickness is the distance between the front and rear faces, said thickness defining a distance said medical workstation mounting apparatus extends from the shelf when installed on said shelf, a plurality of accessory receivers extending from the body, each accessory receiver comprising a pair of arms defining therebetween a channel configured to receive a hook of an accessory, said bods further including a protruding region extending forward from the rear face and defining a generally rectangular channel between the body and said shelf when the apparatus is installed on said shelf, wherein the apparatus has a maximum thickness which is less than its maximum depth.

2. The medical workstation mounting apparatus as claimed in claim I. wherein each arm comprises a proximal portion extending forward of the body and a distal portion extending parallel to the body.

3. The medical workstation mounting apparatus as claimed in claim 2. wherein the distal portion of each arm extends towards the distal portion of the other arm of the pair.

4. The medical workstation mounting apparatus as claimed in claim 3, wherein a slot is defined between the distal ends of the arms, in communication with the channel.

5. The medical workstation mounting apparatus as claimed in claim 1, wherein all the edges and corners of the apparatus are radiussed or chamfered.

6. The medical workstation mounting apparatus as claimed in claim 1, wherein two accessory receivers are provided, located at opposite ends of the elongate body.

7. The medical workstation mounting apparatus as claimed in claim 1, comprising a plurality of openings in the elongate body to receive mechanical fixing devices.

8. The medical workstation mounting apparatus as claimed in claim 1, wherein the protruding region protrudes forward no further than the accessory receivers.

9. The medical workstation mounting apparatus as claimed in claim 1, formed as an integral moulding.

10. A medical workstation mounting apparatus comprising a trolley with at least one shelf, and the medical workstation mounting apparatus as claimed in claim 1 attached to the shelf.

* * * * *